United States Patent [19]

Bandman et al.

[11] Patent Number: 5,955,301

[45] Date of Patent: Sep. 21, 1999

[54] HUMAN GLUTAMATE-BINDING PROTEIN

[75] Inventors: Olga Bandman; Roger Coleman, both of Mountain View, Calif.

[73] Assignee: Incyte Pharmaceuticals, Inc., Palo Alto, Calif.

[21] Appl. No.: 08/749,289

[22] Filed: Nov. 14, 1996

[51] Int. Cl.$^6$ .......................... C12N 15/00; C12N 15/12; C12N 15/11; C07K 14/00

[52] U.S. Cl. .................... 435/69.1; 435/91.2; 435/240.2; 435/252.3; 435/320.1; 536/23.1; 536/24.32; 536/23.4; 530/350; 935/1; 935/19; 935/52

[58] Field of Search ................................ 536/23.1, 24.32, 536/23.4; 435/240.2, 252.3, 91.2, 320.1, 69.1; 530/350; 935/1, 19, 52

[56] References Cited

U.S. PATENT DOCUMENTS 4,800,159  1/1989  Mullin et al. .

OTHER PUBLICATIONS

Misun, W., et al., "Identification of human liver cDNA clones whose products interact with G–protein beta," Chemical Abstracts, vol. 126, No. 8, 1997, Columbus, Ohio, US, Abstract No. 100864, XP002060807.

EMBL nucleotide database, EBI, Hixton, AC: U44954, Aug. 1, 1998, Won, M., et al., Human NMDA Receptor Glutamate–Binding Chain (hnfgw) mRNA, partial cds, XP002060852.

Bliss et al., "A synaptic model of memory: long–term potentiation in the hippocampus," *Nature*, 361:31–39 (1993).

Moriyoshi et al., "Molecular cloning and characterization of the rat NMDA receptor," *Nature*, 354:31–37 (1991).

Hollmann et al., "Zinc Potentiates Agonist–Induced Currents at Certain Splice Variants of the NMDA Receptor," *Neutron*, 10:943–954 (1993).

Foldes et al., "Cloning and sequence analysis of cDNAs encoding human hippocampus N–methyl–D–aspartate receptor subunits: evidence for alternative RNA splicing," *Gene*, 131:293–298 (1993).

Nakanishi, "Molecular Diversity of Glutamate Receptors and Implications for Brain Function," *Science*, 258:597–603.

Kumar et al., "Cloning of cDNA for the glutamate–binding subunit of an NMDA receptor complex," *Nature*, 354:70–73 (GI 112064).

Masoed et al Mol. Pharmacol. 1994 45 (2),324–9.

*Primary Examiner*—Paula K. Hutzell
*Assistant Examiner*—Khalid Masood
*Attorney, Agent, or Firm*—Lucy J. Billings; Incyte Pharmaceuticals, Inc.

[57] ABSTRACT

The present invention provides a human glutamate-binding protein (HGLUBP) and polynucleotides which identify and encode HGLUBP. The invention also provides genetically engineered expression vectors and host cells comprising the nucleic acid sequences encoding HGLUBP and a method for producing HGLUBP. The invention also provides for use of HGLUBP and agonists, antibodies, or antagonists specifically binding HGLUBP, in the prevention and treatment of diseases associated with expression of HGLUBP. Additionally, the invention provides for the use of antisense molecules to polynucleotides encoding HGLUBP for the treatment of diseases associated with the expression of HGLUBP. The invention also provides diagnostic assays which utilize the polynucleotide, or fragments or the complement thereof, and antibodies specifically binding HGLUBP.

6 Claims, 9 Drawing Sheets

```
                                9              18          27          36          45          54
5' CAC GCG TCC GGC GCA TCC GAG CGT GGC CGC CTC GGG GGC GGA CCG CGG AAC CCG 63          72          81          90          99         108
AGG CCA TGT CCC ATG AAA AGA GTT TTT TGG TGT CTG GGG ACA ACT ATC CTC CCC
         .       M   K   R   V   F   W   C   L   G   T   T   I   L   P 117         126         135         144         153         162
CCA ACC CTG GAT ATC CGG GGG GGC CCC AGC CAC CCA TGC CCC CCT ATG CTC AGC
 P   T   L   D   I   R   G   G   P   S   H   P   C   P   P   M   L   S 171         180         189         198         207         216
CTC CCT ACC CTG GGG CCC CTT ACC CAC AGC CCC CTT TCC AGC CCC CCT CCT ACG
 L   P   T   L   G   P   L   T   H   S   P   L   S   S   P   P   P   T 225         234         243         252         261         270
GTC AGC CAG GGT ACC CCC ATG GCC CCA GCC CCT ACC CCC AAG GGG GCT ACC CAC
 V   S   Q   G   T   P   M   A   P   A   P   T   P   K   G   A   T   H 279         288         297         306         315         324
AGG GTC CCT ACC CCC AAG GGG GCT ACC CAC AGG GGC CCC TAC CCA CAA GAG GGC
 R   V   P   T   P   K   G   A   T   H   R   G   P   Y   P   Q   E   G 333         342         351         360         369         378
TAC CCA CAG GGC CCC TAC CCC CAA GGG GGC TAC CCC CAG GGG CCA TAT CCC CAG
 Y   P   Q   G   P   Y   P   Q   G   G   Y   P   Q   G   P   Y   P   Q
```

FIGURE 1A

```
    387              396              405              414              423              432
AGC CCC TTC CCC CCC AAC CCC TAT GGA CAG CCA CAG GTC TTC CCA GGA CAA GAC
 S   P   F   P   P   N   P   Y   G   Q   P   Q   V   F   P   G   Q   D 441              450              459              468              477              486
CCT GAC TCA CCC CAG CAT GGA AAC TAC CAG GAG GAG GGT CCC CCA TCC TAC TAT
 P   D   S   P   Q   H   G   N   Y   Q   E   E   G   P   P   S   Y   Y 495              504              513              522              531              540
GAC AAC CAG GAC TTC CCT GCC ACC AAC TGG GAT GAC AAG AGC ATC CGA CAG GCC
 D   N   Q   D   F   P   A   T   N   W   D   D   K   S   I   R   Q   A 549              558              567              576              585              594
TTC ATC CGC AAG GTG TTC CTA GTG TTC CAG CTG ACC TTG TCG ACC CTG TCC
 F   I   R   K   V   F   L   V   F   Q   L   T   L   S   V   T   L   S 603              612              621              630              639              648
ACG GTG TCT GTG TTC ACT TTT GTT GCG GAG GTG TTC TTC ATC TCT CGG GAG AAT
 T   V   S   V   F   T   F   V   A   E   V   F   F   I   S   L   R   E   N 657              666              675              684              693              702
GTC TGG ACC TAC GTC TAT GTC TCC TAT GCT GTC TTC TTC ATC TCT CTC ATC GTC CTC
 V   W   T   Y   V   Y   V   S   Y   A   V   F   F   I   S   L   I   V   L 711              720              729              738              747              756
AGC TGT TGT GGG GAC TTC CGG CGA AAG CAC CCC TGG AAC CTT GTT GCA CTG TCG
 S   C   C   G   D   F   R   R   K   H   P   W   N   L   V   A   L   S
```

FIGURE 1B

```
                765              774              783              792              801              810
GTC CTG ACC GCC AGC CTG TCG TAC ATG GTG GGG ATG ATC GCC AGC TTC TAC AAC
 V   L   T   A   S   L   S   Y   M   V   G   M   I   A   S   F   Y   N 819              828              837              846              855              864
ACC GAG GTC ATC ATG GCC GTG ACC CGC ATC GGC ATC ACA GCC GTC TTC ACC GTC
 T   E   V   I   M   A   V   T   R   I   G   I   T   A   V   F   T   V 873              882              891              900              909              918
GTC ATC TTC TCC ATG CAG ACC CGC TAC GAC TTC ACC TCA TGC ATG GGC GTG CTC
 V   I   F   S   M   Q   T   R   Y   D   F   T   S   C   M   G   V   L 927              936              945              954              963              972
CTG GTG AGC ATG GTG GTG CTC TTC ATC TTC GCC ATT CTC TGC CTC TTC ATC CGG
 L   V   S   M   V   V   L   F   I   F   A   I   L   C   L   F   I   R 981              990              999              1008             1017             1026
AAC CGC ATC CTG GAG ATC GTG TAC GCC TCA CTG GGG GCT CTG CTC TTC ACC TGC
 N   R   I   L   E   I   V   Y   A   S   L   G   A   L   L   F   T   C 1035             1044             1053             1062             1071             1080
TTC CTC GCA GTG GAC ACC CAG CTG CTG CTG GGG AAC AAG CAG CTG TCC CTG AGC
 F   L   A   V   D   T   Q   L   L   L   G   N   K   Q   L   S   L   S 1089             1098             1107             1116             1125             1134
CCA GAA GAG TAT GTG TTT GCT GCG CTG AAC CTG TAC ACA GAC ATC ATC AAC ATC
 P   E   E   Y   V   F   A   A   L   N   L   Y   T   D   I   I   N   I
```

FIGURE 1C

```
      1143            1152            1161            1170            1179            1188
TTC CTG TAC ATC CTC ACC ATC ATT GGC CGC GCC AAG GAG TAG CCG AGC TCC AGC
 F   L   Y   I   L   T   I   I   G   R   A   K   E 1197,           1206            1215            1224            1233            1242
TCG CTG TGC CCG CTC AGG TGG CAC GGC TGG CCT GGA CCC TGC CCC TGG CAC GGC 1251            1260            1269            1278            1287            1296
AGT GCC AGC TGT ACT TCC CCT CTC TCT TGT CCC CAG GCA CAG CCT AGG GAA AAG 1305            1314            1323            1332            1341            1350
GAT GCC TCT CTC CAA CCC TCC TGT ATG TAC ACT GCA GAT ACT TCC ATT TGG ACC 1359            1368            1377            1386            1395            1404
CGC TGT GGC CAC AGC ATG GCC CCT TTA GTC CTC CCG CCC CCG CCA AGG GGC ACC 1413            1422            1431            1440            1449            1458
AAG GCC ACG TTT CCG TGC CAC CTC CTG TCT ACT CAT TGT TGC ATG AGC CCT GTC 1467            1476            1485            1494            1503            1512
TGC CAG CCC ACC CCA GGG ACT GGG GCC AGC ACC AGG TCC CGG GGA GAG GGA TTG
```

FIGURE 1D

```
     1521            1530            1539            1548            1557           1566
AGC CAA GAG GTG CAC GTC TTC CCT CCT GTC CCA GCT CCC CAG CCT GGC 1575            1584            1593            1602            1611           1620
GTA GAG CAC CCC TCC CCT CCC CCC CAC CCC CCT GGA GTG CTG CCC TCT GGG GAC 1629            1638            1647            1656            1665           1674
ATG CGG AGT GGG GKT CTT ATC CCT GTG CTG AGC CCT GAG GGC AGA GAG GAT GGC 1683            1692            1701            1710            1719           1728
ATG TTT CAG GGG AGG GGG AAG CCT TCC TCT CAA TTT GTT GTC AGT GAA ATT CCA 1737            1746            1755
ATA AAT GGG ATT TGC TCT CTG CCA AAA AAA AAA AAA AAA AAA  3'
```

FIGURE 1E

```
1   MKRVFWCLGTTILPPTLDIRGGPSHPCPPMLSLPTLGPLT  386116
1   MKRVSWSLGTAILPQTLAILWGHKPLCLPMFSLPTLGPHT  gi112064

41  HSPLSSPPPTVSQGTPMAPAPTPKGATHRVPTP---KGAT  386116
41  HRPLSSPLPMVNQGIPMVPVPI----TRWLPLKDLLKEAT  gi112064

78  HRGPYPQEGYPQGPYPQGGYPQGPYPQSPFPPNPYGQPQV  386116
77  H---------------------QGHYPQSPFPPNPYGQPPP  gi112064

118 FPGQDPDSPQHGNYQEEGPPSYYDNQDFPATNWDDKSIRQ  386116
97  F--QDPGSPQHGNYQEEGPPSYYDNQDFPSVNWD-KSIRQ  gi112064

158 AFIRKVFLVLTLQLSVTLSTVSVFTFVAEVKGFVRENVWT  386116
134 AFIRKVFLVLTLQLSVTLSTVAIFTFVGEVKGFVRANVWT  gi112064

198 YYVSYAVFFISLIVLSCCGDFRRKHPWNLVALSVLTASLS  386116
174 YYVSYAIFFISLIVLSCCGDFRKKHPWNLVALSILTISLS  gi112064

238 YMVGMIASFYNTEAVIMAVGITTAVCFTVVIFSMQTRYDF  386116
214 YMVGMIASFYNTEAVIMAVGITTAVCFTVVIFSMQTRYDF  gi112064
```

HUMAN GLUTAMATE-BINDING PROTEIN

FIELD OF THE INVENTION

This invention relates to nucleic acid and amino acid sequences of a novel human glutamate-binding protein and to the use of these sequences in the diagnosis, prevention, and treatment of disorders and diseases of the central nervous system, defects in motor rhythms, vasomotor tone, and baroreception, as well as for muscle relaxation and sedation.

BACKGROUND OF THE INVENTION

L-Glutamic and L-aspartic acids (so-called excitatory amino acids) are the most common neurotransmitters in the brain and have extremely powerful excitatory effects throughout the central nervous system (CNS). Binding of an excitatory amino acid to an ionotropic receptor causes the opening of a cation-selective channel. The ionotropic receptors are multi-subunit proteins that are further subclassified on the basis of binding to agonists which selectively activate a specific receptor subtype. Such agonists include α-amino-3-hydroxy-5-methyl-4-isoxazole proprionic acid (AMPA), kainate, and N-methyl-D-aspartate (NMDA).

Pre-synaptic release of glutamate causes an excitatory post-synaptic current which can be resolved into fast and slow (long-lasting) components. The slow component is mediated by NMDA-gated ion channels and has characteristic features including a slow rise and decay of the current and high $Ca^{2+}$ permeability. NMDA receptors are involved in the development of long-term potentiation (LTP), a long-lasting increase in size of the post-synaptic response to a pre-synaptic stimulus of fixed strength. LTP has been proposed as a model for learning and memory (Bliss, T. V. and G. L. Collingridge, Nature (1993) 361:31–39).

NMDA receptors are expressed in virtually every neuronal cell in the body. They are composed of a core subunit that forms a homomeric channel when expressed heterologously. The activity of the core subunit is modified and/or regulated by coexpression of the other subunits. Various cDNAs encoding NMDA channel subunits have been cloned and expressed from rat (Moriyoshi, K. et al. (1991) Nature 354:31–37; Hollmann, M. J. et al. (1993) Neuron 10:943–954) and human (Foldes, R. L. et al. (1993) Gene 131:293–298). Some of the subunit isoforms are encoded by separate genes, whereas others arise by alternative mRNA splicing, and perhaps by RNA editing. Functional diversity can also arise by coexpression of multiple forms of the same subunit in a single cell. The molecular diversity of NMDA receptors has been reviewed by S. Nakanishi (1992; Science 258:597–603).

The NMDA receptor complex must have a binding site for the natural ligand, glutamate, and the cDNA for a glutamate-binding component of an NMDA receptor has been cloned from rat (Kumar, K. N. et al. (1991) Nature 354:70–73). Binding sites for glycine (co-agonist), $Zn^{2+}$ (modulatory factor), polyamine (activator), and $Mg^{2+}$ (voltage-dependent blocker) have also been identified on the multimeric NMDA channel complex.

High concentrations of extracellular glutamate arise, for example, after stroke or hypoglycemia. Exposure of neurons to a high concentration of glutamate, even for short periods, causes cell death and disease. Excessive activation of NMDA receptors leads to an influx of abnormally large amounts of $Ca^{2+}$ into the cell. Toxicity and neuronal death can be mediated by stimulation of downstream pathways which may include activation of gene expression, protein kinases, proteases, and apoptosis (programmed cell death). Neurodegenerative diseases may also be caused by the overexpression and/or inappropriate expression of NMDA receptors.

Discovery of molecules related to the glutamate-binding subunit of the NMDA receptor satisfies a need in the art by providing new diagnostic or therapeutic compositions useful in the diagnosis, prevention, and treatment of conditions and diseases affecting the CNS such as ischemia, hypoglycemia, epilepsy, convulsions, AIDS-related dementia, schizophrenia, chronic neurodegenerative disorders such as Alzheimer's, Huntington's, Creutzfeld-Jacob, and Parkinson's disease, amyotrophic lateral sclerosis, and lathyrism, chronic and neuropathic pain, and defects in motor rhythms, vasomotor tone, baroreception, and LTP, as well as muscle relaxation and sedation.

SUMMARY OF THE INVENTION

The present invention features a novel human glutamate-binding protein hereinafter designated HGLUBP and characterized as having chemical and structural homology to the rat glutamate-binding subunit of the NMDA receptor. Accordingly, the invention features a substantially purified HGLUBP having the amino acid sequence shown, SEQ ID NO:1.

One aspect of the invention features isolated and substantially purified polynucleotides that encode HGLUBP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HGLUBP. The present invention also features antibodies which bind specifically to HGLUBP, and pharmaceutical compositions comprising substantially purified HGLUBP. The invention also features the use of agonists and antagonists of HGLUBP.

BRIEF DESCRIPTION OF THE FIGURES

FIGS. 1A, 1B, 1C, 1D and 1E show the amino acid sequence (SEQ ID NO:1) and nucleic acid sequence (SEQ ID NO:2) of HGLUBP. The alignment was produced using MACDNASIS PRO™ software (Hitachi Software Engineering Co., Ltd., San Bruno, Calif.).

FIGS. 2A and 2B show the amino acid sequence alignment between HGLUBP (SEQ ID NO:1), and the rat glutamate-binding subunit of the NMDA receptor (GI112064; SEQ ID NO:3). The alignment was produced using the multisequence alignment program of DNASTAR software (DNASTAR Inc., Madison Wis.).

DESCRIPTION OF THE INVENTION

Figure 3:
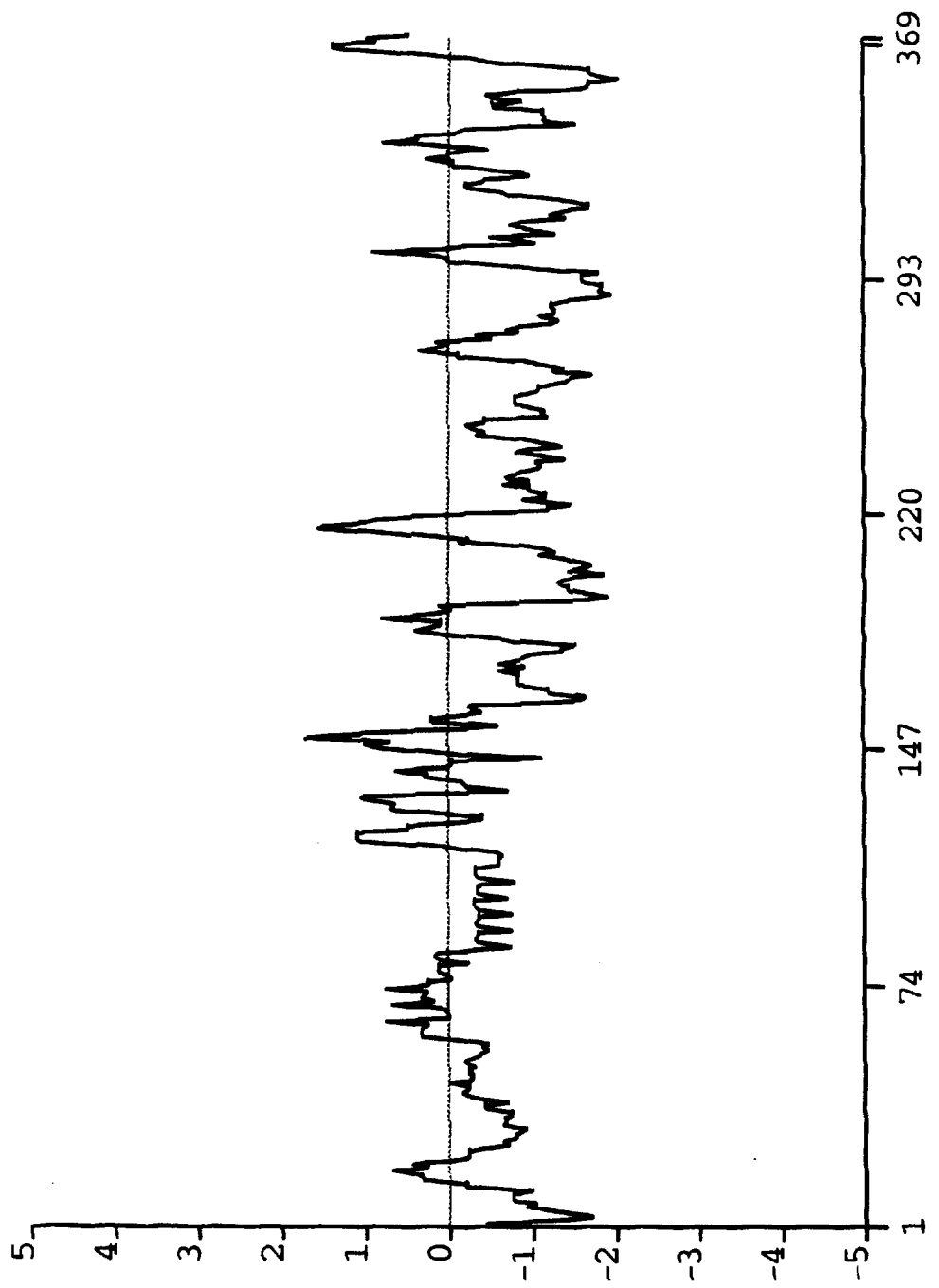
FIG. 3 shows the hydrophobicity plot (MACDNASIS PRO software) for HGLUBP (SEQ ID NO:1). The positive X axis reflects amino acid position, and the negative Y axis reflects hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HGLUBP, as used herein, refers to the amino acid sequences of substantially purified HGLUBP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™(Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of HGLUBP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HGLUBP, or any oligopeptide thereof, to induce a specific immune response in appropriate animals or cells and to bind with specific antibodies.

The term "agonist", as used herein, refers to a molecule which, when bound to HGLUBP, causes a change in HGLUBP which modulates the activity of HGLUBP. Agonists may include proteins, nucleic acids, carbohydrates, or any other molecules which bind to HGLUBP.

The terms "antagonist" or "inhibitor", as used herein, refer to a molecule which, when bound to HGLUBP, modulates or blocks the biological or immunological activity of HGLUBP. Antagonists and inhibitors may include proteins, nucleic acids, carbohydrates, or any other molecules which bind to HGLUBP.

The term "modulate", as used herein, refers to a change or an alteration in the biological activity of HGLUBP. Modulation may be an increase or a decrease in protein activity, a change in binding characteristics, or any other change in the biological, functional or immunological properties of HGLUBP.

The term "mimetic", as used herein, refers to a molecule, the structure of which is developed from knowledge of the structure of HGLUBP or portions thereof and, as such, is able to effect some or all of the actions of the glutamate-binding subunit of NMDA receptor-like molecules.

The term "derivative", as used herein, refers to the chemical modification of a nucleic acid encoding HGLUBP or the encoded HGLUBP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HGLUBP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HGLUBP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding HGLUBP in a sample and thereby correlates with expression of the transcript from the polynucleotide encoding the protein.

"Alterations" in the polynucleotide of SEQ ID NO:2, as used herein, comprise any alteration in the sequence of polynucleotides encoding HGLUBP including deletions, insertions, and point mutations that may be detected using hybridization assays. Included within this definition is the detection of alterations to the genomic DNA sequence which encodes HGLUBP (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding HGLUBP (e.g., using fluorescent in situ hybridization (FISH) to metaphase chromosomes spreads).

As used herein, the term "antibody" refers to intact molecules as well as fragments thereof, such as Fab F(ab')$_2$, and Fv, which are capable of binding the epitopic determinant. Antibodies that bind HGLUBP polypeptides can be prepared using intact polypeptides or fragments containing small peptides of interest as the immunizing antigen. The polypeptide or peptide used to immunize an animal can be derived from translated RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human glutamate-binding protein (HGLUBP), the polynucleotides encoding HGLUBP, and the use of these compositions for the diagnosis, prevention or treatment of conditions and diseases affecting the central nervous system (CNS) such as ischemia, hypoglycemia, epilepsy, convulsions, AIDS-related dementia, schizophrenia, chronic neurodegenerative disorders such as Alzheimer's, Huntington's, Creutzfeld-Jacob, and Parkinson's disease, amyotrophic lateral sclerosis, and lathyrism, chronic and neuropathic pain, and defects in motor rhythms, vasomotor tone, baroreception, and long term potentiation (LTP), as well as muscle relaxation and sedation.

Nucleic acids encoding the HGLUBP of the present invention were first identified in Incyte Clone 386116 from the thymus cDNA library (THYMNOT02) through a computer-generated search for amino acid sequence alignments. A consensus sequence, SEQ ID NO:2, was derived from the overlapping and/or extended nucleic acid sequences of Incyte Clones 386116 (THYMNOT02), 267670 (HNT2NOT01), 381752 (HYPONOB01), and 754894 (BRAITUT02).

In one embodiment, the invention encompasses the novel human glutamate-binding protein, a polypeptide comprising the amino acid sequence of SEQ ID NO:1, as shown in FIGS. 1A, 1B, 1C, 1D, and 1E. HGLUBP is 369 amino acids in length and has a hydrophobic N-terminal sequence that is characteristic of a signal peptide. HGLUBP has no predicted sites for N-linked glycosylation, but has five potential sites for O-linked glycosylation on threonine residues. HGLUBP has chemical and structural homology with the rat glutamate binding protein, GI112064 (SEQ ID NO:3) (Kumar et al., supra) as shown in FIGS. 2A, and 2B. In particular, HGLUBP (SEQ ID NO:1) and GI112064 (SEQ ID NO:3) share 72% identity. The nucleotide sequence (SEQ ID NO:2) predicts that HGLUBP (SEQ ID NO:1) is 147 amino acids shorter than the rat homolog GI112064 (SEQ ID NO:3), with the difference being primarily at the carboxy-terrninus of the protein. These differences may represent species differences between human and rat, and/or novel differences in their functions.

Figure 4:
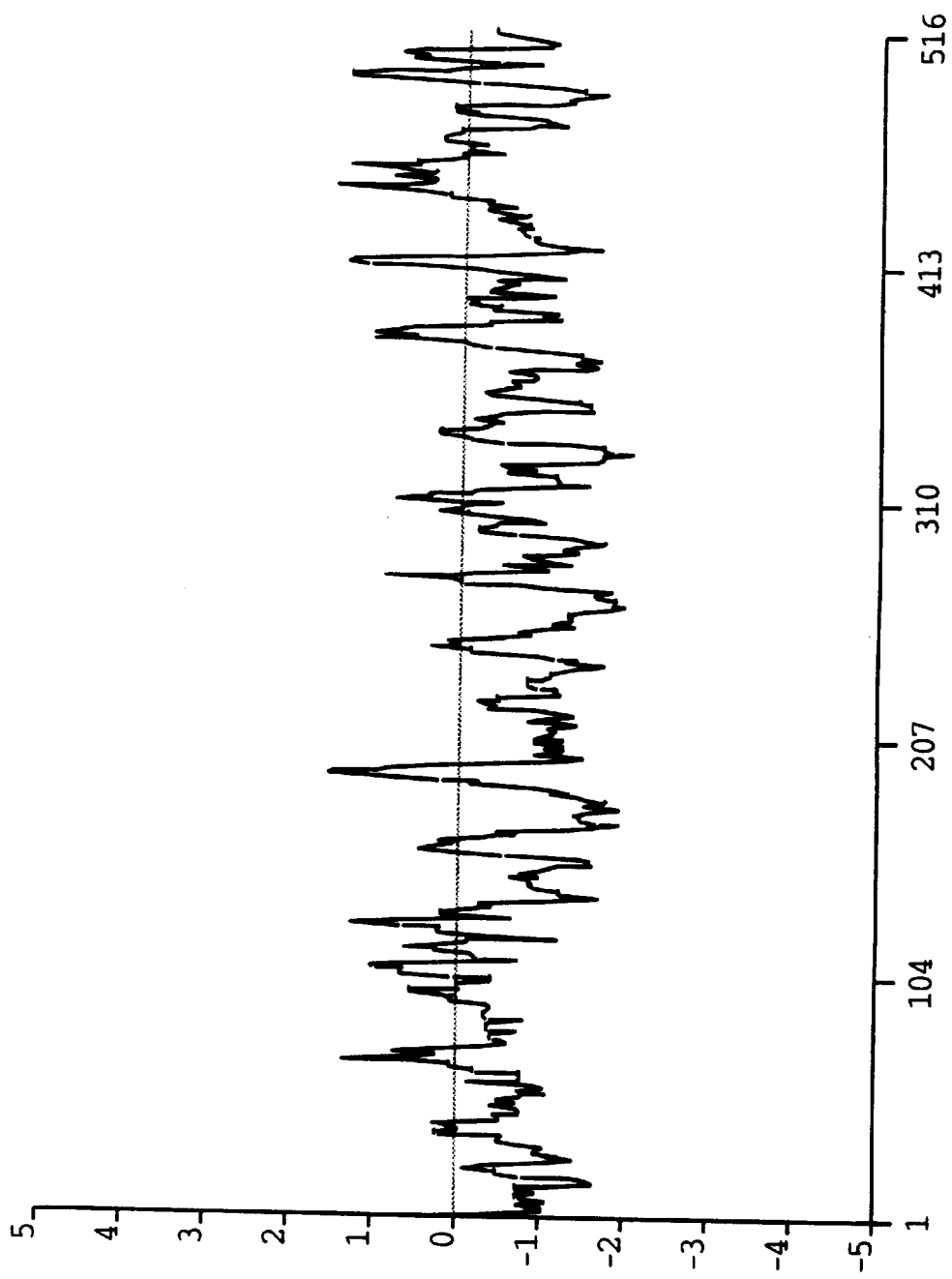
FIG. 4 shows the hydrophobicity plot for the rat glutamate-binding subunit of the NMDA receptor (SEQ ID NO:3).

There is a high degree of homology between each of the four predicted transmembrane regions of HGLUBP (residues 178–201, 211–230, 260–285, and 297–320, respectively, of SEQ ID NO:1) and the corresponding region of the rat protein GI112064 (SEQ ID NO:3). As illustrated by FIGS. 3 and 4, HGLUBP and GI112064 have similar hydrophobicities in the region of sequence homology which suggests that they have similar structures.

The invention also encompasses HGLUBP variants. A preferred HGLUBP variant is one having at least 80%, and more preferably 90%, amino acid sequence similarity to the HGLUBP amino acid sequence (SEQ ID NO:1). A most preferred HGLUBP variant is one having at least 95% amino acid sequence similarity to SEQ ID NO:1.

The invention also encompasses polynucleotides which encode HGLUBP. Accordingly, any nucleic acid sequence which encodes the amino acid sequence of HGLUBP can be used to generate recombinant molecules which express HGLUBP. In a particular embodiment, the invention encompasses the polynucleotide comprising the nucleic acid of SEQ ID NO:2 as shown in FIGS. 1A, 1B, 1C, 1D, and 1E.

It will be appreciated by those skilled in the art that as a result of the degeneracy of the genetic code, a multitude of nucleotide sequences encoding HGLUBP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HGLUBP, and all such variations are to be considered as being specifically disclosed.

Although nucleotide sequences which encode HGLUBP and its variants are preferably capable of hybridizing to the nucleotide sequence of the naturally occurring HGLUBP under appropriately selected conditions of stringency, it may be advantageous to produce nucleotide sequences encoding HGLUBP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HGLUBP and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HGLUBP and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HGLUBP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Kimmel, A. R. (1987; Methods Enzymol. Vol. 152), and may be used at a defined stringency.

Altered nucleic acid sequences encoding HGLUBP which are encompassed by the invention include deletions, insertions, or substitutions of different nucleotides resulting in a polynucleotide that encodes the same or a functionally equivalent HGLUBP. The encoded protein may also contain deletions, insertions, or substitutions of amino acid residues which produce a silent change and result in a functionally equivalent HGLUBP. Deliberate amino acid substitutions may be made on the basis of similarity in polarity, charge, solubility, hydrophobicity, hydrophilicity, and/or the amphipathic nature of the residues as long as the biological activity of HGLUBP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding HGLUBP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the Hamilton MICROLAB 2200 (Hamilton, Reno, Nev.), Peltier Thermal Cycler (PTC200; M.J. Research, Watertown, Mass.) and the ABI 377 DNA sequencers (Perkin Elmer).

The polynucleotide sequence encoding HGLUBP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nuc. Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111 –119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nuc. Acids Res. 19:3055–3060). Additionally, one may use PCR, nested primers, and PROMOTERFINDER libraries to walk in genomic DNA (Clontech, Palo Alto, Calif.). This process avoids the need to screen libraries and may be is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HGLUBP, or fusion proteins or functional equivalents thereof, may be used in recombinant DNA molecules to direct expression of HGLUBP in appropriate host cells. Due to the inherent degeneracy of the genetic code, other DNA sequences which encode substantially the same or a functionally equivalent amino acid sequence may be produced and these sequences may be used to clone and express HGLUBP.

As will be understood by those of skill in the art, it may be advantageous to produce HGLUBP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HGLUBP coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding HGLUBP may be ligated to a heterologous sequence to encode a fusion protein. For example, to screen peptide libraries for inhibitors of HGLUBP activity, it may be useful to encode a chimeric HGLUBP protein that can be recognized by a commercially available antibody. A fusion protein may also be engineered to contain a cleavage site located between a HGLUBP encoding sequence and the heterologous protein sequence, so that HGLUBP may be cleaved and purified away from the heterologous moiety.

In another embodiment, the coding sequence of HGLUBP may be synthesized, in whole or in part, using chemical methods well known in the art (see Caruthers, M. H. et al. (1980) Nuc. Acids Res. Symp. Ser. 215–223, Horn, T. et al. (1980) Nuc. Acids Res. Symp. Ser. 225–232). Alternatively, the protein itself may be produced using chemical methods to synthesize the HGLUBP amino acid sequence, or a portion thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles*, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of HGLUBP, or any part thereof, may be altered during direct synthesis and/or combined using chemical methods with sequences from other proteins, or any part thereof, to produce a variant polypeptide.

In order to express a biologically active HGLUBP, the nucleotide sequence encoding HGLUBP or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HGLUBP coding sequence and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express a HGLUBP coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSport™ plasmid (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HGLUBP, vectors based on SV40 or EBV may be used with an appropriate selectable marker.

In bacterial systems, a number of expression vectors may be selected depending upon the use intended for HGLUBP. For example, when large quantities of HGLUBP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding HGLUBP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding HGLUBP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express HGLUBP. For example, in one such system, *Autographa californica* nuclear polyhedrosis virus (AcNPV) is used as a vector to express foreign genes in *Spodoptera frugiperda* cells or in Trichoplusia larvae. The sequence encoding HGLUBP may be cloned into a non-essential region of the virus, such as the polyhedrin gene, and placed under control of the polyhedrin promoter. Successful insertion of HGLUBP will render the polyhedrin gene inactive and produce recombinant virus lacking coat protein. The recombinant viruses may then be used to infect, for example, *S. frugiperda* cells or Trichoplusia larvae in which HGLUBP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, a sequence encoding HGLUBP may be ligated into an adenovirus transcription/translation complex consisting of the late promoter and tripartite leader sequence. Insertion in a non-essential E1 or E3 region of the viral genome may be used to obtain a viable virus which is capable of expressing HGLUBP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of a sequence encoding HGLUBP. Such signals include the ATG initiation codon and adjacent sequences. In cases where sequences encoding HGLUBP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HGLUBP may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–232) and adenine phosphoribosyltransferase (Lowy, I. et al. (1980) Cell 22:817–823) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–3570); npt, which confers resistance to the aminoglycosides neomycin and G-418 (Colbere-Garapin, F. et al. (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–8051). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HGLUBP is inserted within a marker gene sequence, recombinant cells containing sequences encoding HGLUBP can be identified by the absence of marker gene function. Alternatively, a marker gene can be placed in tandem with a sequence encoding HGLUBP under the control of a single promoter. Expression of the marker gene in response to induction or selection usually indicates expression of the tandem gene as well.

Alternatively, host cells which contain the coding sequence for HGLUBP and express HGLUBP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of the nucleic acid or protein.

The presence of the polynucleotide sequence encoding HGLUBP can be detected by DNA-DNA or DNA-RNA hybridization or amplification using probes or portions or fragments of polynucleotides encoding HGLUBP. Nucleic acid amplification based assays involve the use of oligonucleotides or oligomers based on the HGLUBP-encoding sequence to detect transformants containing DNA or RNA encoding HGLUBP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HGLUBP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HGLUBP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HGLUBP include oligolabeling, nick translation, end-labeling or PCR amplification using a labeled nucleotide. Alternatively, the sequence encoding HGLUBP, or any portion of it, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding HGLUBP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HGLUBP may be designed to contain signal sequences which direct secretion of HGLUBP through a prokaryotic or eukaryotic cell membrane. Other recombinant constructions may be used to join sequences encoding HGLUBP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immnunex Corp., Seattle, Wash.). The inclusion of cleavable linker sequences such as those specific for Factor XA or enterokinase (Invitrogen, San Diego, Calif.) between the purification domain and HGLUBP may be used to facilitate purification. One such expression vector provides for expression of a fusion protein containing HGLUBP and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263–281) while the enterokinase cleavage site provides a means for purifying HGLUBP from the fusion protein. A discussion of vectors which contain fusion proteins is provided in Kroll, D. J. et al. (1993; DNA Cell Biol. 12:441–453).

In addition to recombinant production, fragments of HGLUBP may be produced by direct peptide synthesis using solid-phase techniques (cf Stewart et al. (1969) *Solid-Phase Peptide Synthesis*, W. H. Freeman Co., San Francisco, Calif.; MERRIFIELD, J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of HGLUBP may be chemically synthesized separately and combined using chemical methods to produce the full length molecule.

THERAPEUTICS

Based on the chemical and structural homology between HGLUBP (SEQ ID NO:1) and the rat glutamate-binding protein and northern analysis which shows a high percent abundance of HGLUBP in CNS tissues including immortalized cells and diseased tissue therefrom, as well as breast, endocrine glands, and lung, HGLUBP is believed to function in nerve impulse conduction as the glutamate-binding protein of post-synaptic NMDA receptors a vector expressing it, In one embodiment, HGLUBP, or a fragment or derivative thereof, may be administered to a subject to treat disorders of the central nervous system wherein an increased response to signaling by glutamate is desirable. Such conditions and diseases may include, but are not limited to, defects in motor rhythms, nociception, baroreception, vasomotor tone, and LTP.

In another embodiment, a vector capable of expressing HGLUBP, or a fragment or a derivative thereof, may be administered to a subject to treat disorders of the central nervous system, as noted above, wherein an increased response to signaling by glutamate is desirable.

In another embodiment, vectors expressing antisense of the polynucleotides encoding HGLUBP, or antagonists or inhibitors of HGLUBP may be administered to a subject to prevent or treat neuronal damage resulting from high concentrations of extracellular glutamate. Such conditions and diseases include, but are not limited to, ischemia, hypoglycemia, epilepsy, convulsions, AIDS-related dementia, schizophrenia, Alzheimer's and Parkinson's disease, amyotrophic lateral sclerosis, and lathyrism. Antagonists or inhibitors of HGLUBP may also be administered to a subject to induce muscle relaxation or sedation.

In another embodiment, antagonists which block or modulate the effect of HGLUBP may be used in other situations where such inhibition is therapeutically desirable. Such antagonists or inhibitors may be produced using methods which are generally known in the art. A particular method involes the use of purified HGLUBP to screen libraries of pharmaceutical agents in order to identify those which specifically bind HGLUBP.

Antibodies which are specific for HGLUBP may be used directly as an antagonist, or indirectly as a targeting or delivery mechanism for bringing a pharmaceutical agent to cells or tissues which express HGLUBP. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HGLUBP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium paryum* are especially preferable.

It is preferred that the peptides, fragments, or oligopeptides used to induce antibodies to HGLUBP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HGLUBP amino acids may be fused with those of another protein such as keyhole limpet hemocyanin and antibody produced against the chimeric molecule.

Monoclonal antibodies to HGLUBP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used ((Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HGLUBP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HGLUBP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HGLUBP and its specific antibody. A two-site, monoclonal-based immunoassay utilizing monoclonal antibodies reactive to two non-interfering HGLUBP epitopes is preferred, but a competitive binding assay may also be employed (Maddox, supra).

In another embodiment of the invention, the polynucleotides encoding HGLUBP, or any fragment thereof, or antisense sequences, may be used for therapeutic purposes. In one aspect, antisense to the polynucleotide encoding HGLUBP may be used in situations in which it would be desirable to block the synthesis of the protein. In particular, cells may be transformed with sequences complementary to polynucleotides encoding HGLUBP. Thus, antisense sequences may be used to modulate HGLUBP activity, or to achieve regulation of gene function. Such technology is now well known in the art, and sense or antisense oligomers or larger fragments, can be designed from various locations along the coding or control regions of sequences encoding HGLUBP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HGLUBP. These techniques are described both in Sambrook et al. (supra) and in Ausubel et al. (supra).

Genes encoding HGLUBP can be turned off by transforming a cell or tissue with expression vectors which express high levels of a polynucleotide or fragment thereof which encodes HGLUBP. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HGLUBP, i.e., the promoters, enhancers, and introns. Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HGLUBP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HGLUBP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl phosphodiester linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo in vitro. and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HGLUBP, antibodies to HGLUBP, mimetics, agonists, antagonists, or inhibitors of HGLUBP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HGLUBP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HGLUBP or fragments thereof, antibodies of HGLUBP, agonists, antagonists or inhibitors of HGLUBP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio ED50/LD50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HGLUBP may be used for the diagnosis of conditions or diseases characterized by expression of HGLUBP, or in assays to monitor patients being treated with HGLUBP, agonists, antagonists or inhibitors. The antibodies useful for diagnostic purposes may be prepared in the same manner as those described above for therapeutics. Diagnostic assays for HGLUBP include methods which utilize the antibody and a label to detect HGLUBP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HGLUBP are known in the art and provide a basis for diagnosing altered or abnormal levels of HGLUBP expression. Normal or standard values for HGLUBP expression are established by combining body fluids or cell extracts taken from normal mammalian subjects, preferably human, with antibody to HGLUBP under conditions suitable for complex formation. The amount of standard complex formation may be quantified by various methods, preferably by photometric means. Quantities of HGLUBP expressed in subject samples from biopsied tissues are compared with the standard values. Deviation between standard and subject values establishes the parameters for diagnosing disease.

In another embodiment of the invention, the polynucleotides encoding HGLUBP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HGLUBP may be correlated with disease. The diagnostic assay may be used to distinguish between absence, presence, and excess expression of HGLUBP, and to monitor regulation of HGLUBP levels during therapeutic intervention.

In one aspect, hybridization with PCR probes which are capable of detecting polynucleotide sequences, including genomic sequences, encoding HGLUBP or closely related molecules, may be used to identify nucleic acid sequences which encode HGLUBP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HGLUBP, alleles, or related sequences.

Probes may also be used for the detection of related sequences, and should preferably contain at least 50% of the nucleotides from any of the HGLUBP encoding sequences. The hybridization probes of the subject invention may be DNA or RNA and derived from the nucleotide sequence of SEQ ID NO:2 or from genomic sequence including promoter, enhancer elements, and introns of the naturally occurring HGLUBP.

Means for producing specific hybridization probes for DNAs encoding HGLUBP include the cloning of nucleic acid sequences encoding HGLUBP or HGLUBP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HGLUBP may be used for the diagnosis of conditions or diseases which are associated with expression of HGLUBP. Examples of such conditions or diseases include ischemia, hypoglycemia, epilepsy, convulsions, AIDS-related dementia, schizophrenia, chronic neurodegenerative disorders such as Alzheimer's, Huntington's, Creutzfield-Jacob, and Parkinson's disease, amyotrophic lateral sclerosis, and lathyrism, as well as pain, both chronic and neuropathic, and defects in motor rhythms, vasomotor tone, baroreception, and long-term potentiation. The polynucleotide sequences encoding HGLUBP may be used in Southern or northern analysis, dot blot, or other membrane-based technologies; in PCR technologies; or in dip stick, pin, ELISA or chip assays utilizing fluids or tissues from patient biopsies to detect altered HGLUBP expression. Such qualitative or quantitative methods are well known in the art.

The nucleotide sequence encoding HGLUBP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding HGLUBP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HGLUBP, a normal or standard profile for expression is established. This may be accomplished by combining body fluids or cell extracts taken from normal subjects, either animal or human, with a sequence, or a fragment thereof, which encodes HGLUBP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for oligonucleotides encoding HGLUBP may involve the use of PCR. Such oligomers may be chemically synthesized, generated enzymatically, or produced from a recombinant source. Oligomers will preferably consist of two nucleotide sequences, one with sense orientation (5→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HGLUBP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212–229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequence which encodes HGLUBP may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HGLUBP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HGLUBP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HGLUBP and the agent being tested, may be measured.

Another technique for drug screening which may be used provides for high throughput screening of compounds having suitable binding affinity to the protein of interest as described in published PCT application WO84/03564. In this method, as applied to HGLUBP large numbers of different small test compounds are synthesized on a solid substrate, such as plastic pins or some other surface. The test compounds are reacted with HGLUBP, or fragments thereof, and washed. Bound HGLUBP is then detected by methods well known in the art. Purified HGLUBP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HGLUBP specifically compete with a test compound for binding HGLUBP. In this manner, the antibodies can be used to detect the presence of any peptide which shares one or more antigenic determinants with HGLUBP.

In additional embodiments, the nucleotide sequences which encode HGLUBP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I TYMNOT02 cDNA Library Construction

The THYMNOT02 library was constructed from the thymus tissue of a three year old Caucasian male (lot #93–122) obtained from the Keystone Skin Bank, International Institute for the Advancement of Medicine (Exton, Pa.). The frozen tissue was ground in a mortar and pestle and lysed immediately in a buffer containing guanidinium isothiocyanate. The lysate was extracted twice with phenol chloroform at pH 8.0 and centrifuged over a CsCl cushion using a Beckman SW28 rotor in a Beckman L8-70Multracentrifuge (Beckman Instruments, Fullerton, Calif.). The RNA was precipitated using 0.3M sodium acetate and 2.5 volumes of ethanol, resuspended in water and DNase treated for 15 min at 37° C. The RNA was isolated using the OLIGOTEX kit (QIAGEN Inc, Chatsworth, Calif.) and used to construct the cDNA library.

First strand cDNA synthesis was accomplished using an oligo d(T) primer/linker which also contained an Xho I restriction site. Second strand synthesis was performed using a combination of DNA polymerase I, E. coli ligase and RNase H, followed by the addition of an Eco RI adaptor to the blunt ended cDNA. The Eco RI adapted, double-stranded cDNA was then digested with Xho I restriction enzyme and fractionated on Sephacryl S400 to obtain sequences which exceeded 1000 bp in size. The size selected cDNAs were inserted into the LAMBDAZAP vector system (Stratagene); and the vector, which contains the PBLUE-SCRIPT phagemid (Stratagene), was transformed into cells of XL1-BLUEMRF E. coli strain (Stratagene).

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid DNA molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Isolation and Sequencing of cDNA Clones

Plasmid DNA was purified using the Miniprep Kit (Cat. #77468, Advanced Genetic Technologies Corporation, Gaithersburg Md.), a 96-well block kit with reagents for 960 purifications. The recommended protocol included with the kit was employed except for the following changes. Each of the 96 wells was filled with only 1 ml of sterile Terrific Broth (Cat. #22711, LIFE TECHNOLOGIES) with carbenicillin at 25 mg/l and glycerol at 0.4%. After the wells were inoculated, the bacteria were cultured for 24 hours and lysed with 60 μl of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger F. and A. R. Coulson (1975; J. Mol. Biol. 94:441f), using a Hamilton MICROLAB 2200 (Hamilton, Reno, Nev.) in combination with four Peltier Thermal Cyclers (PTC200 from M.J. Research, Watertown, Mass.) and Applied Biosystems 377 or 373 DNA sequencing systems (Perkin Elmer) and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul S. F. (1993) J. Mol. Evol. 36:290–300; Altschul, S. F. et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the minimum length of the sequences in the Sequence Listing is 49 nucleotides, and the upper limit of uncalled bases where N is recorded rather than A, C, G, or T is 12%.

The BLAST approach, as detailed in Karlin and Altschul (1993; Proc. Natl. Acad. Sci. 90:5873–5877) and incorporated herein by reference, searches matches between a query sequence and a database sequence, to evaluate the statistical significance of any matches found, and to report only those matches which satisfy the user-selected threshold of significance. In this application, threshold was set at 10–25 for nucleotides and 10–14 for peptides.

Incyte nucleotide sequence were searched against the GenBank databases for primate, rodent, and mammalian sequences, and deduced amino acid sequences from the same clones are searched against GenBank functional protein databases, mammalian, vertebrate and eukaryote, for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ FL database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity x % maximum BLAST score 100
The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HGLUBP occurs. Abundance and percent abundance are also reported. Abundance directly reflects the number of times a particular transcript is represented in a cDNA library, and percent abundance is abundance divided by the total number of sequences examined in the cDNA library.

V Extension of HGLUBP-Encoding Polynucleotides to Full Length or to Recover Regulatory Sequences Full length HGLUBP-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2x Carb. The following day, several colonies are randomly picked from each plate and cultured in 150 µl of liquid LB/2x Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer, and one or both of the gene specific primers used for the extension reaction are added to each well. Amplification is performed using the following conditions:

Step 1 94° C. for 60 sec

Step 2 94° C. for 20 sec

Step 3 55° C. for 30 sec

Step 4 72° C. for 90 sec

Step 5 Repeat steps 2–4 for an additional 29 cycles

Step 6 72° C. for 180 sec

Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba I, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots, or the blots are exposed in a Phosphoimager cassette (Molecular Dynamics, Sunnyvale, Calif.), hybridization patterns are compared visually.

VII Antisense Molecules

Antisense molecules to the HGLUBP-encoding sequence, or any part thereof, is used to inhibit in vivo or in vitro expression of naturally occurring HGLUBP. Although use of antisense oligonucleotides, comprising about 20 base-pairs, is specifically described, essentially the same procedure is used with larger cDNA fragments. An oligonucleotide based on the coding sequences of HGLUBP, as shown in FIGS. 1A, 1B, 1C, 1D and 1E, is used to inhibit expression of naturally occurring HGLUBP. The complementary oligonucleotide is designed from the most unique 5' sequence as shown in FIGS. 1A and 1B and used either to inhibit transcription by preventing promoter binding to the upstream nontranslated sequence or translation of an HGLUBP-encoding transcript by preventing ribosome binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIG. 1A and 1B.

VIII Expression of HGLUBP

Expression of HGLUBP is accomplished by subcloning the cDNAs into appropriate vectors and transforming the vectors into host cells. In this case, the cloning vector, PSPORT(Gibro BRL), previously used for the generation of the cDNA library is used to express HGLUBP in E. coli. Upstream of the cloning site, this vector contains a promoter for $\beta$-galactosidase, followed by sequence containing the amino-terminal Met, and the subsequent seven residues of $\beta$-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of $\beta$-galactosidase, about 5 to 15 residues of linker, and the full length protein. The signal residues direct the secretion of HGLUBP into the bacterial growth media which can be used directly in the following assay for activity.

IX Demonstration of HGLUBP Activity

HGLUBP can be expressed by transforming a mammalian cell line such as COS7, HeLa or CHO with an eukaryotic expression vector encoding HGLUBP. Eukaryotic expression vectors are commercially available and the techniques to introduce them into cells are well known to those skilled in the art. The cells are incubated for 48–72 hours after transformation under conditions appropriate for the cell line to allow expression and accumulation of HGLUBP.

Membranes are prepared from the transformed cells by techniques well known in the art. Portions of the membrane preparation are incubated with 5–50 $\mu$Ci of [$^3$H]-glutamate under suitable conditions of pH and ionic strength. The ligand is allowed to bind to the membranes for 5–30 minutes before the sample is filtered through a nitrocellulose filter having a 0.2 m$\mu$ pore size (Millipore Corp., Bedford, Mass.). The filters are washed with cold buffer to remove unbound ligand, dried, and then immersed in a commercially available scintillation fluid prior to counting in a liquid scintillation counter (Beckman Instruments, Fullerton, Calif.). Binding levels can be compared with those of membranes extracted from control, untransformed cells or from cells transformed with vector alone.

X Production of HGLUBP Specific Antibodies

HGLUBP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc.) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HGLUBP Using Specific Antibodies

Naturally occurring or recombinant HGLUBP is substantially purified by immunoaffinity chromatography using antibodies specific for HGLUBP. An immunoaffinity column is constructed by covalently coupling HGLUBP antibody to an activated chromatographic resin, such as CnBr-activated SEPHANOSE (Pharmacia & Upjohn). After the coupling, the resin is blocked and washed according to the manufacturer's instructions.

Media containing HGLUBP is passed over the immunoaffinity column, and the column is washed under conditions that allow the preferential absorbance of HGLUBP (e.g., high ionic strength buffers in the presence of detergent). The column is eluted under conditions that disrupt antibody/HGLUBP binding (e.g., a buffer of pH 2–3 or a high concentration of a chaotrope, such as urea or thiocyanate ion), and HGLUBP is collected.

XII Identification of Molecules Which Interact with HGLUBP

HGLUBP or biologically active fragments thereof are labeled with $^{125}$I-Bolton-Hunter reagent (Bolton et al. (1973) Biochem. J. 133:529). Candidate molecules previously arrayed in the wells of a multi-well plate are incubated with the labeled HGLUBP, washed and any wells with labeled HGLUBP complex are assayed. Data obtained using different concentrations of HGLUBP are used to calculate values for the number, affinity, and association of HGLUBP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. An isolated and purified polynucleotide sequence comprising SEQ ID NO:2.

3. An isolated and purified polynucleotide sequence which is fully complementary to SEQ ID NO:2.

4. An expression vector containing the polynucleotide sequence of claim 1.

5. A host cell containing the expression vector of claim 4.

6. A method for producing a polypeptide comprising SEQ ID NO:1, the method comprising the steps of:

a) culturing the host cell of claim 5 under conditions suitable for the expression of the polypeptide; and b) recovering the polypeptide from the host cell culture.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 369 amino acids
      (B) TYPE: amino acid
      (C) STRANDEDNESS: single
      (D) TOPOLOGY: linear (vii) IMMEDIATE SOURCE:
      (A) LIBRARY: Consensus
      (B) CLONE: 386116

(xi) SEQUENCE DESCRIPTION: SEQ ID NO:1:

```
Met Lys Arg Val Phe Trp Cys Leu Gly Thr Thr Ile Leu Pro Pro Thr
 1               5                  10                  15

Leu Asp Ile Arg Gly Gly Pro Ser His Pro Cys Pro Pro Met Leu Ser
            20                  25                  30

Leu Pro Thr Leu Gly Pro Leu Thr His Ser Pro Leu Ser Ser Pro Pro
        35                  40                  45

Pro Thr Val Ser Gln Gly Thr Pro Met Ala Pro Ala Pro Thr Pro Lys
    50                  55                  60

Gly Ala Thr His Arg Val Pro Thr Pro Lys Gly Ala Thr His Arg Gly
65                  70                  75                  80

Pro Tyr Pro Gln Glu Gly Tyr Pro Gln Gly Pro Tyr Pro Gln Gly Gly
                85                  90                  95

Tyr Pro Gln Gly Pro Tyr Pro Gln Ser Pro Phe Pro Pro Asn Pro Tyr
            100                 105                 110

Gly Gln Pro Gln Val Phe Pro Gly Gln Asp Pro Asp Ser Pro Gln His
            115                 120                 125

Gly Asn Tyr Gln Glu Glu Gly Pro Pro Ser Tyr Tyr Asp Asn Gln Asp
        130                 135                 140

Phe Pro Ala Thr Asn Trp Asp Asp Lys Ser Ile Arg Gln Ala Phe Ile
145                 150                 155                 160

Arg Lys Val Phe Leu Val Leu Thr Leu Gln Leu Ser Val Thr Leu Ser
                165                 170                 175
```

```
Thr Val Ser Val Phe Thr Phe Val Ala Glu Val Lys Gly Phe Val Arg
        180                 185                 190
Glu Asn Val Trp Thr Tyr Tyr Val Ser Tyr Ala Val Phe Phe Ile Ser
            195                 200                 205
Leu Ile Val Leu Ser Cys Cys Gly Asp Phe Arg Arg Lys His Pro Trp
            210                 215                 220
Asn Leu Val Ala Leu Ser Val Leu Thr Ala Ser Leu Ser Tyr Met Val
225                 230                 235                 240
Gly Met Ile Ala Ser Phe Tyr Asn Thr Glu Ala Val Ile Met Ala Val
                245                 250                 255
Gly Ile Thr Thr Ala Val Cys Phe Thr Val Ile Phe Ser Met Gln
            260                 265                 270
Thr Arg Tyr Asp Phe Thr Ser Cys Met Gly Val Leu Leu Val Ser Met
        275                 280                 285
Val Val Leu Phe Ile Phe Ala Ile Leu Cys Ile Phe Ile Arg Asn Arg
        290                 295                 300
Ile Leu Glu Ile Val Tyr Ala Ser Leu Gly Ala Leu Leu Phe Thr Cys
305                 310                 315                 320
Phe Leu Ala Val Asp Thr Gln Leu Leu Leu Gly Asn Lys Gln Leu Ser
                325                 330                 335
Leu Ser Pro Glu Glu Tyr Val Phe Ala Ala Leu Asn Leu Tyr Thr Asp
                340                 345                 350
Ile Ile Asn Ile Phe Leu Tyr Ile Leu Thr Ile Ile Gly Arg Ala Lys
                355                 360                 365
Glu (2) INFORMATION FOR SEQ ID NO:2:

(i) SEQUENCE CHARACTERISTICS:
        (A) LENGTH: 1770 base pairs
        (B) TYPE: nucleic acid
        (C) STRANDEDNESS: single
        (D) TOPOLOGY: linear (vii) IMMEDIATE SOURCE:
        (A) LIBRARY: Consensus
        (B) CLONE: 386116

(xi) SEQUENCE DESCRIPTION: SEQ ID NO:2:

CACGCGTCCG GCGCATCCGA GCGTGGCCGC CTCGGGGGCG GACCGCGGAA CCCGAGGCCA     60

TGTCCCATGA AAAGAGTTTT TTGGTGTCTG GGGACAACTA TCCTCCCCCC AACCCTGGAT    120

ATCCGGGGGG GCCCCAGCCA CCCATGCCCC CCTATGCTCA GCCTCCCTAC CCTGGGGCCC    180

CTTACCCACA GCCCCCTTTC CAGCCCTCCC CCTACGGTCA GCCAGGGTAC CCCCATGGCC    240

CCAGCCCCTA CCCCCAAGGG GGCTACCCAC AGGGTCCCTA CCCCCAAGGG GGCTACCCAC    300

AGGGGCCCCT ACCCACAAGA GGGCTACCCA CAGGGCCCCT ACCCCCAAGG GGGCTACCCC    360

CAGGGGCCAT ATCCCCAGAG CCCCTTCCCC CCAACCCCT ATGGACAGCC ACAGGTCTTC    420

CCAGGACAAG ACCCTGACTC ACCCCAGCAT GGAAACTACC AGGAGGAGGG TCCCCCATCC    480

TACTATGACA ACCAGGACTT CCCTGCCACC AACTGGGATG ACAAGAGCAT CCGACAGGCC    540

TTCATCCGCA AGGTGTTCCT AGTGCTGACC TTGCAGCTGT CGGTGACCCT GTCCACGGTG    600

TCTGTGTTCA CTTTTGTTGC GGAGGTGAAG GGCTTTGTCC GGGAGAATGT CTGGACCTAC    660

TATGTCTCCT ATGCTGTCTT CTTCATCTCT CTCATCGTCC TCAGCTGTTG TGGGGACTTC    720

CGGCGAAAGC ACCCCTGGAA CCTTGTTGCA CTGTCGGTCC TGACCGCCAG CCTGTCGTAC    780

ATGGTGGGGA TGATCGCCAG CTTCTACAAC ACCGAGGCAG TCATCATGGC CGTGGGCATC    840
```

```
ACCACAGCCG TCTGCTTCAC CGTCGTCATC TTCTCCATGC AGACCCGCTA CGACTTCACC    900

TCATGCATGG GCGTGCTCCT GGTGAGCATG GTGGTGCTCT TCATCTTCGC CATTCTCTGC    960

ATCTTCATCC GGAACCGCAT CCTGGAGATC GTGTACGCCT CACTGGGCGC TCTGCTCTTC   1020

ACCTGCTTCC TCGCAGTGGA CACCCAGCTG CTGCTGGGGA CAAGCAGCT GTCCCTGAGC   1080

CCAGAAGAGT ATGTGTTTGC TGCGCTGAAC CTGTACACAG ACATCATCAA CATCTTCCTG   1140

TACATCCTCA CCATCATTGG CCGCGCCAAG GAGTAGCCGA GCTCCAGCTC GCTGTGCCCG   1200

CTCAGGTGGC ACGGCTGGCC TGGACCCTGC CCCTGGCACG GCAGTGCCAG CTGTACTTCC   1260

CCTCTCTCTT GTCCCCAGGC ACAGCCTAGG GAAAAGGATG CCTCTCTCCA ACCCTCCTGT   1320

ATGTACACTG CAGATACTTC CATTTGGACC CGCTGTGGCC ACAGCATGGC CCCTTTAGTC   1380

CTCCCGCCCC CGCCAAGGGG CACCAAGGCC ACGTTTCCGT GCCACCTCCT GTCTACTCAT   1440

TGTTGCATGA GCCCTGTCTG CCAGCCCACC CCAGGGACTG GGGGCAGCAC CAGGTCCCGG   1500

GGAGAGGGAT TGAGCCAAGA GGTGAGGGTG CACGTCTTCC CTCCTGTCCC AGCTCCCCAG   1560

CCTGGCGTAG AGCACCCCTC CCCTCCCCCC CACCCCCCTG GAGTGCTGCC CTCTGGGGAC   1620

ATGCGGAGTG GGGKTCTTAT CCCTGTGCTG AGCCCTGAGG GCAGAGAGGA TGGCATGTTT   1680

CAGGGGAGGG GGAAGCCTTC CTCTCAATTT GTTGTCAGTG AAATTCCAAT AAATGGGATT   1740

TGCTCTCTGC CAAAAAAAAA AAAAAAAAA                                     1770

(2) INFORMATION FOR SEQ ID NO:3:

(i) SEQUENCE CHARACTERISTICS:
        (A) LENGTH: 516 amino acids
        (B) TYPE: amino acid
        (C) STRANDEDNESS: double
        (D) TOPOLOGY: linear (xi) SEQUENCE DESCRIPTION: SEQ ID NO:3:

Met Lys Arg Val Ser Trp Ser Leu Gly Thr Ala Ile Leu Pro Gln Thr
 1               5                  10                  15

Leu Ala Ile Leu Trp Gly His Lys Pro Leu Cys Leu Pro Met Phe Ser
            20                  25                  30

Leu Pro Thr Leu Gly Pro His Thr His Arg Pro Leu Ser Ser Pro Leu
        35                  40                  45

Pro Met Val Asn Gln Gly Ile Pro Met Val Pro Val Pro Ile Thr Arg
    50                  55                  60

Trp Leu Pro Leu Lys Asp Leu Leu Lys Glu Ala Thr His Gln Gly His
65                  70                  75                  80

Tyr Pro Gln Ser Pro Phe Pro Pro Asn Pro Tyr Gly Gln Pro Pro Pro
                85                  90                  95

Phe Gln Asp Pro Gly Ser Pro Gln His Gly Asn Tyr Gln Glu Glu Gly
            100                 105                 110

Pro Pro Ser Tyr Tyr Asp Asn Gln Asp Phe Pro Ser Val Asn Trp Asp
        115                 120                 125

Lys Ser Ile Arg Gln Ala Phe Ile Arg Lys Val Phe Leu Val Leu Thr
    130                 135                 140

Leu Gln Leu Ser Val Thr Leu Ser Thr Val Ala Ile Phe Thr Phe Val
145                 150                 155                 160

Gly Glu Val Lys Gly Phe Val Arg Ala Asn Val Trp Thr Tyr Tyr Val
                165                 170                 175

Ser Tyr Ala Ile Phe Phe Ile Ser Leu Ile Val Leu Ser Cys Cys Gly
            180                 185                 190
```

-continued

```
Asp Phe Arg Lys Lys His Pro Trp Asn Leu Val Ala Leu Ser Ile Leu
        195                 200                 205

Thr Ile Ser Leu Ser Tyr Met Val Gly Met Ile Ala Ser Phe Tyr Asn
        210                 215                 220

Thr Glu Ala Val Ile Met Ala Val Gly Ile Thr Thr Ala Val Cys Phe
225                     230                 235                 240

Thr Val Val Ile Phe Ser Met Gln Thr Arg Tyr Asp Phe Thr Ser Cys
                245                 250                 255

Met Gly Val Leu Leu Val Ser Val Val Leu Phe Ile Phe Ala Ile
                260                 265                 270

Leu Cys Ile Phe Ile Arg Asn Arg Ile Leu Glu Ile Val Tyr Ala Ser
                275                 280                 285

Leu Gly Ala Leu Leu Phe Thr Cys Phe Leu Ala Val Asp Thr Gln Leu
        290                 295                 300

Leu Leu Gly Asn Lys Gln Leu Ser Leu Ser Pro Glu Glu Tyr Val Phe
305                     310                 315                 320

Ala Ala Leu Asn Leu Tyr Thr Asp Ile Ile Asn Ile Phe Leu Tyr Ile
                325                 330                 335

Leu Thr Ile Ile Gly Arg Ser Gln Gly Ile Gly Gln Ala Pro Ala Gln
                340                 345                 350

Val Ala Trp Trp Ala Gln Thr His Ala Pro Gly Met Thr Leu Pro Ser
        355                 360                 365

Val Leu Pro Pro Leu Trp Phe Pro Ala Met Ala Trp Ser Arg Gly Ser
        370                 375                 380

Pro Ser Arg Pro Arg Val Cys Thr Leu Gln Ile Leu Asn Val Arg Thr
385                     390                 395                 400

Leu Ser Ala Thr Ala Trp Lys Pro Leu Ser Leu Leu Pro Leu Pro Arg
                405                 410                 415

Gly Asp Arg Ala Ala Phe Leu Cys His Leu Leu Ser Thr His Cys Cys
                420                 425                 430

Met Ser Pro Val Cys Gln Pro Ile Pro Gly Ser Gly Ile Asn Thr Arg
        435                 440                 445

Ser Gln Gly Arg Arg Ile Ile Pro Arg Gly Glu Gly Ala Arg Leu Pro
        450                 455                 460

Ser Cys Pro Ser Ser Pro Gly Ile Glu Ser Pro Cys Pro Leu Leu Thr
465                     470                 475                 480

Leu Pro Ser Glu Gly Leu Ala Gly Trp Gly Leu Val Leu Val Leu Gly
                485                 490                 495

Pro Glu Thr Lys Arg Gly Trp His Val Ser Gly Glu Arg Leu Ser Cys
                500                 505                 510

Val Leu Pro Leu
        515
```